United States Patent [19]

Black et al.

[11] Patent Number: 4,571,444

[45] Date of Patent: Feb. 18, 1986

[54] PROCESS FOR SEPARATING ALKYLAROMATICS FROM AROMATIC SOLVENTS AND THE SEPARATION OF THE ALKYLAROMATIC ISOMERS USING MEMBRANES

[75] Inventors: Laura E. Black; Heather A. Boucher, both of Sarnia, Canada

[73] Assignee: Exxon Research and Engineering Co., Florham Park, N.J.

[21] Appl. No.: 603,028

[22] Filed: Apr. 27, 1984

[51] Int. Cl.[4] .......................................... C07G 7/144
[52] U.S. Cl. .................................... 585/819; 208/308
[58] Field of Search ...................... 210/638, 654, 637; 585/819, 446; 208/308

[56] References Cited

U.S. PATENT DOCUMENTS

| | | | |
|---|---|---|---|
| 2,923,749 | 2/1960 | Lee et al. | 260/674 |
| 2,930,754 | 3/1960 | Stuckey | 210/23 |
| 2,947,687 | 8/1960 | Lee | 210/23 |
| 2,958,657 | 11/1960 | Binning et al. | 210/23 |
| 2,970,106 | 1/1961 | Binning et al. | 208/347 |
| 2,981,680 | 4/1961 | Binning | 210/23 |
| 2,985,588 | 5/1961 | Binning et al. | 210/23 |
| 3,043,891 | 7/1962 | Stuckey | 260/674 |
| 3,140,256 | 7/1964 | Martin et al. | 210/23 |
| 3,225,107 | 12/1965 | Kirkland et al. | 260/652 |
| 3,228,876 | 1/1966 | Mahon | 210/22 |
| 3,305,595 | 2/1967 | Paulson | 260/674 |
| 3,370,102 | 2/1968 | Carpenter et al. | 260/674 |
| 3,504,048 | 3/1970 | de Rosset | 260/674 |
| 3,556,991 | 1/1971 | Gerhold | 208/321 |
| 3,720,321 | 3/1973 | Coughlin et al. | 210/550 |
| 3,776,970 | 12/1973 | Strazik et al. | 585/819 |
| 3,789,079 | 1/1974 | Perry et al. | 260/681.5 |
| 3,853,754 | 12/1974 | Gosser | 210/23 |
| 3,919,075 | 11/1975 | Parc et al. | 208/180 |
| 3,930,990 | 1/1976 | Brun et al. | 208/308 |
| 4,062,882 | 12/1977 | Gupta | 260/428.5 |
| 4,113,628 | 9/1978 | Alegranti | 210/500 |
| 4,115,465 | 9/1978 | Elfert et al. | 260/674 |
| 4,154,770 | 5/1979 | Kaplan | 585/332 |
| 4,301,317 | 10/1981 | Young | 585/467 X |

FOREIGN PATENT DOCUMENTS

| | | |
|---|---|---|
| 0013834 | 6/1980 | European Pat. Off. . |
| 99426 | 6/1983 | Japan ........................... 585/819 |
| 1435151 | 5/1976 | United Kingdom . |
| 1434639 | 5/1976 | United Kingdom . |
| 2051664A | 1/1981 | United Kingdom . |
| 2073654A | 10/1981 | United Kingdom . |
| 2116071A | 9/1983 | United Kingdom . |

OTHER PUBLICATIONS

"Separation of Aromatics and Naphthenens by Permeating Through Modified Vinylidene Fluoride Films", McCandless, Ind. Eng. Chem. Process. Des. Develop., vol. 12, #3, 1973, pp. 354–359.

"Regeneration of Used Lubricating Oils by Ultrafiltration", Defives, et al., Information Chemie #175, pp. 127–131, Mar. 1978.

"New Polyimide Ultrafiltration Membranes for Organic Use", Iwama, et al., Journal of Membrane Science II (1982) 297–309.

Primary Examiner—John Doll
Assistant Examiner—Glenn A. Caldarola
Attorney, Agent, or Firm—Joseph J. Allocca

[57] ABSTRACT

In the production of alkylaromatics by the alkylation of aromatic hydrocarbons with alkylating agents such as olefins typically in the presence of a catalyst, the unconverted aromatic hydrocarbon remaining after completion of the alkylation process is separated from the alkylaromatic product and the terminal alkylaromatic isomers are separated from the mixture of alkylaromatic isomers produced in the alkylation process by the selective permeation of the aromatic hydrocarbon and the terminal isomers through a permselective membrane, preferably an asymmetric membrane producing a permeate rich in the terminal isomers and a retentate which is lean (i.e., depleated) in the terminal isomers. Permeation is under reverse osmosis conditions, that is, under a pressure sufficient to at least overcome the osmotic pressure of the aromatic hydrocarbon present in the mixture made up of the aromatic hydrocarbon, the olefin and the mixed isomer alkylaromatic product. Permeation is carried out at a pressure of about 100 to 800 psig, preferably a pressure of about 200 to 600 psig, more preferably a pressure of about 300 to 500 psig, at a temperature of about 0° to 100° C., preferably about 20°–80° C., most preferably about 20° to 50° C. The membrane of choice is an asymmetric polyimide membrane.

14 Claims, 1 Drawing Figure

INTEGRATION OF MEMBRANE UNIT WITH ALKYLATION PROCESS
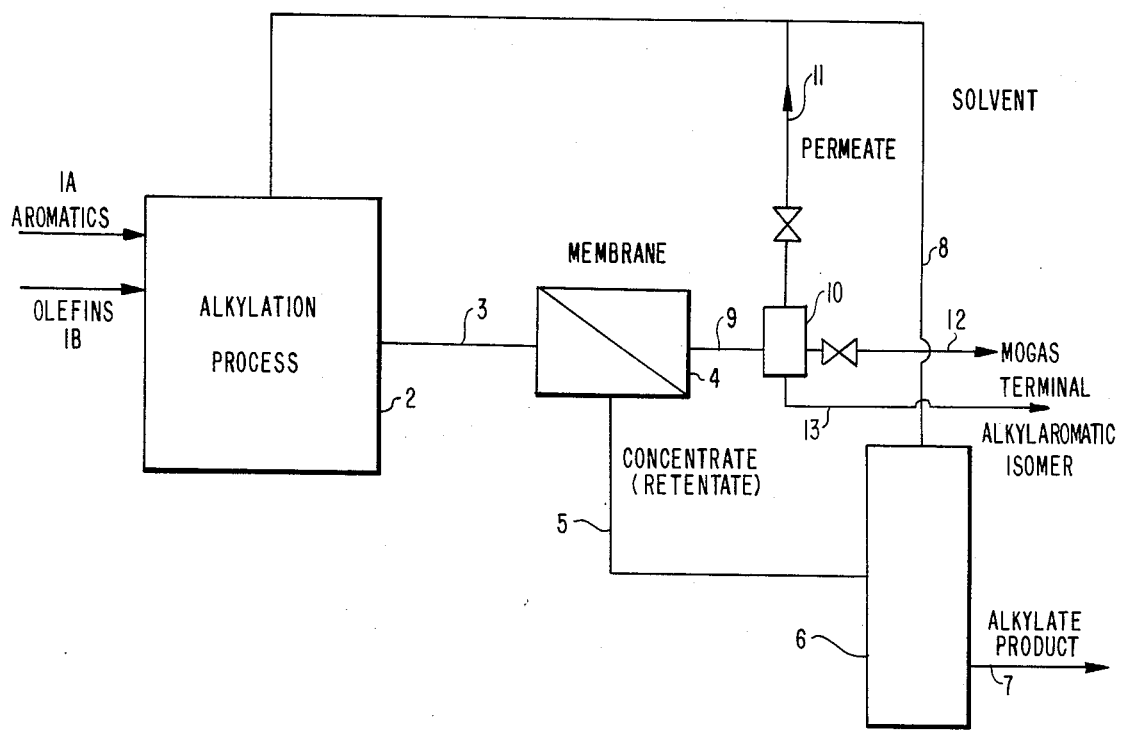
FIG. I

PROCESS FOR SEPARATING ALKYLAROMATICS FROM AROMATIC SOLVENTS AND THE SEPARATION OF THE ALKYLAROMATIC ISOMERS USING MEMBRANES

DESCRIPTION OF THE INVENTION

Alkylaromatics are produced by contacting an alkylating agent, such as an olefin, with an aromatic hydrocarbon, such as benzene, toluene, xylene, naphthalene, etc. The resulting alkylaromatic product stream typically contains mono-, di- and tri-alkylated aromatic products, olefinic dimers, as well as unconsumed alkylating agent and aromatic hydrocarbon starting materials. The alkylated aromatic product, to be useful, must be recovered from this mixed stream and it is often desirable that the alkylaromatic itself be separated into its different isomers. Typically, unconsumed starting materials are separated from products by distillation. Distillation is an energy intensive step and also can result in some deterioration of the materials present in the stream being distilled, e.g., induce polymerization and an accompanying reduction in the yield of desired product.

It would be a great advantage if the alkylation product could be separated, at least partially, from the mixed product/starting material stream by a less energy intensive, less disruptive process than distillation. In addition, it would be useful to be able to effect some separation of the product stream into its isomeric components by a low energy, non-degradative process.

DESCRIPTION OF THE FIGURE

FIG. 1 is a schematic of the integrated process of the present invention.

Selective permeation through a selective membrane, preferably an asymmetric membrane, e.g., asymmetric polyimide, under reverse osmosis conditions has been found to be an effective method for separating unconverted aromatic and olefinic starting material from alkylaromatic products and for the separation of the alkylaromatic into its isomers. The alkylaromatic product stream containing a mixture of aromatic and alkylating agent, e.g. olefinic, starting material and olefin dimer and mono, di and tri alkyl aromatic products are contacted with one side of the membrane under reverse osmosis conditions. Preferably the membrane is an asymmetric membrane. Asymmetric membranes are membranes characterized by possessing a thin, dense skin layer of polymer on a porous backing of the same polymeric material. Asymmetric membranes are typically produced by a procedure involving the following steps. The selected polymer is dissolved in a solvent system, preferably a mixed solvent system, and the resulting casting dope is spread, drawn or otherwise formed into a thin film on some surface, such as glass, polished metal, nylon backing, etc. The cast film is permitted to evaporate for a short time. This evaporation results in the loss of some of the solvent at the exposed surface of the film resulting in the formation of a thin skin. The film is then immersed in a gelation bath which removes the solvent and causes the stable membrane to form. The polymer which existed between the skin and the casting surface is fixed by the gelation bath as a highly porous layer backing the dense thin skin layer.

If the membrane is gelled in water or some other highly polar gelation nonsolvent for the polymer, or contains, e.g. glycerine or glyceride the membrane is preconditioned for use in the present separation process. This preconditioning takes the form of exposing the membrane to a solvent, or series of solvents, of lower polarity than the gelation solvent. For example, the gelled membrane can be exposed to a ketone (e.g. methyl ethyl ketone) followed by toluene. If the membrane contains glycerine or glyceride the solvent sequence can be e.g. water, to wash out the glycerine or glyceride, followed by, e.g. ketone and toluene. This exposure can be under pressure (e.g. pressure permeation) or can constitute a mere soaking of the membrane in the treatment solvent or series of solvents. The membrane is then hydrophobic in nature and suitable for use in the present separation process.

In the process of the present invention it is preferred that the mixed product stream of the alkylation process be contacted with the dense skin side of an asymmetric membrane under the previously stated reverse osmosis conditions. Reverse osmosis conditions typically constitute a pressure at least sufficient to overcome the osmotic pressure of the solvent present in the stream being contacted with the membrane. In the present case the solvents in the mixed stream (the mixed stream comprising aromatic hydrocarbon, alkylating agent, e.g. olefin, olefin dimer, mono- di and tri alkylaromatic) are the aromatic and alkylation agent, e.g. olefinic, hydrocarbons, while the olefin dimer and mono, di and tri alkylaromatics constitute the solute. In the present process the pres-sure employed preferably ranges from about 100 to 800 psig, preferably about 200 to 600 psig, most preferably about 300 to 500 psig. A temperature of about 0° to 100° C., preferably about 20° to 80° C., most preferably about 20° to 50° C. is employed during this contacting. A permeate stream rich in aromatic and olefinic hydrocarbon is recovered while a retentate stream rich in mono, di and tri alkylate and olefinic dimer and of reduced aromatic and olefin content is produced. Permeation through the asymmetric membrane also effects the simultaneous separation and concentration of the terminal alkylaromatic isomer from the mixture of terminal and internal alkylaromatic isomers produced in the alkylation reaction. As used in this specification, the term "terminal" alkylaromatic isomer is meant to include those isomers of very small cross sectional area and include the 2- and 3-isomers, preferably the 2-isomer, while the term "internal" alkylaromatic isomer is meant to include those isomers of large cross sectional area and include the 4- and greater isomers, as well as isomers of branch chain alkylaromatics.

The retentate stream can be sent to distillation units for further processing. Since the stream is of a much reduced aromatic and olefin content the distillation conditions employed can be of a much reduced severity. Alternatively, the retentate stream can be sent to another membrane unit where it is again contacted with the selective membrane to produce another pair of permeate and retentate streams, effecting further separation of aromatics and alkylating agents from products and further concentration of terminal isomers in the permeate stream and internal isomers in the retentate stream. This cascading of retentate streams to subsequent membrane units can be performed any number of times, depending on the ultimate degree of separation desired by the practitioner.

BACKGROUND

Alkylaromatic sulphonates having straight chain alkyl substituents of from about 8 to about 20 carbon atoms are used as surface active agents in the detergent industry. It is known that the position of the aromatic nucleus on the alkyl chain in these molecules can significantly affect its detergent properties; thus, alkylaromatic isomers having the aromatic nucleus located at internal positions on the alkyl chain exhibit improved detergency and wetting characteristics over isomers where the aromatic nucleus is in the 2- or 3 position (that is, near the end of the alkyl side chain). Detergent manufacturers set a maximum specification of 20 weight percent 2-alkylaromatic isomer for their detergent alkylates.

The position of the aromatic nucleus on the alkyl side chain also affects the properties of alkylaromatic synthetic lubricants. In this case, a high concentration of those isomers with the aromatic nucleus near the end of the alkyl side chain, that is, the 2- and 3-isomers, is desirable in that a long alkyl side chain in the molecule causes it to have a high viscosity index.

It is thus desirable to be able to change the isomeric composition of a mixture of alkylaromatic molecules in a non-degradative manner so that isomers can be used in the manner most suited to their molecular structure.

Prior art has reported methods which alter the concentration of the 2-alkylaromatic isomers in a mixture of alkylaromatic isomers. For example, U.S. Pat. No. 4,298,547, teaches that the 2-alkylaromatic content can be decreased by passing a mixture of alkylaromatic isomers over acidic ZSM-type zeolites under cracking conditions. This process causes the selective cracking of the 2-alkylaromatic isomer, yielding a stream rich in the internal alkylaromatic isomers. Of course, the 2-alkylaromatic isomer is destroyed in the process, and so unavailable for further use. The present separation process described herein is nondegradative, allowing the stream rich in the 2-alkylaromatic isomer to be used as desired, and so constitutes a significant improvement over the prior art.

Prior art teaches the use of a membrane pervaporation process to separate hydrocarbon isomers. Examples are given in the literature of the separation of xylene isomers and the separation of trimethyl pentanes from dimethyl hexanes by a pervaporation process. A pervaporation process involves selective solubility in and diffusion through a non-porous membrane. In the examples mentioned, the molecules with the smaller cross sectional area selectively permeated through the membrane. The maximum percent rejection obtained was 20%.

Prior art has reported the rejection of various butyl alcohol isomers in binary alcohol-water solutions using a reverse osmosis pressure driven membrane process. The highly branched isomers have higher rejections than does the straight chain isomer.

The prior art does not report the use of reverse osmosis to separate a mixture of isomers in a carrier solvent, nor does it address the separation of isomers with molecular weights above $C_8$. Reverse osmosis separation of hydrocarbon isomers offers an improvement over pervaporation in that higher fluxes are attained with higher separation factors and no phase change is involved in the membrane process.

THE PRESENT INVENTION

The alkylaromatic mixed isomer product stream, containing the alkylaromatic products, olefin dimer byproducts and unconverted aromatic and alkylating agent starting materials, which serves as the feed in this separation process is produced by the alkylation of simple aromatic molecules, such as benzene, toluene, the xylenes, ethylbenzene, tetralin, naphthalene, etc and mixtures thereof with a long carbon chain alkylating agent, such as an about $C_8$ to $C_{20}$ olefin (both alpha and random internal double bond) and mixtures thereof or other suitable alkylating agents such as alkyl halides etc. (again having alkyl groups of from about $C_8$ to $C_{20}$). Preferably, the alkylating agent is a normal olefin (i.e. straight chain). The preferred aromatics are benzene, toluene and ethyl benzene, while preferred alkylating agents are the $C_8$–$C_{20}$ olefins, more preferably n-$C_8$–$C_{20}$ olefins (alpha and random).

Alkylated aromatics containing a total of about 23 to 28 carbons, preferably 24–26 carbons, most preferably 24 carbons as exemplified by hexadecane ethylbenzene ($C_2H_5C_6H_4$—$C_{16}H_{33}$) are particularly useful as lube oil basestocks or lube additives, as disclosed and claimed in copending application OP-3016, U.S. Ser. No. 603,032, filed even dateherewith.

The aromatic molecules can be alkylated using any of the typical alkylating procedure, including Friedel-Crafts alkylation, etc.

Alkylating procedures also involve the use of acidic zeolites as alkylating catalysts. Typical zeolites, however, produce a mixture of mono-, di-, tri-, and polyalkylaromatic material.

Alternative catalytic procedures involve the use of wide pore acidic amorphous silica-alumina materials as catalyst (disclosed and claimed in copending application OP-2955, U.S. Ser. No. 603,034, filed even date herewith), and the use of low crystallinity, partially collapsed zeolites (disclosed and claimed in copending application OP-2956, U.S. Ser. No. 603,033, filed even date herewith. Use of these two above-identified catalytic procedures produce alkylaromatic mixtures rich in monoalkylated aromatic product.

In practicing the present separation process, the alkylaromatic mixture is contacted with the thin, dense skin of the membrane (the asymmetric layer). This contacting is at a temperature such that the mixture is in the liquid state, and the membrane does not deteriorate, i.e., above the freezing point of the mixture and below the glass transition temperature of the polymer out of which the membrane is made. This temperature preferably ranges between about 0° to 100° C., more preferably 20°–80° C., most preferably about 35°–60° C. As previously stated, the contacting is under reverse osmosis conditions, that is, under a pressure at least sufficient to overcome the osmotic pressure of the system. In general, the pressure will be an applied pressure of between about 100 psig up to the rupture pressure of the membrane, preferably about 100 to 800 psig, more preferably about 400 to 600 psig. The feed to the membrane comprises the alkylated product, unreacted aromatic and alkylating agent starting material and coproduced by products of the reaction, e.g. di, and tri-alkylates and olefinic dimers. The unreacted aromatic starting material serves as a carrier solvent for the isomers in the product stream and facilitates permeation.

In the absence of a carrier solvent pressure permeation (reverse osmosis) could not be used to separate the isomers since the osmotic pressure of the system of pure isomers would be high enough so that no permeation would occur. The carrier solvent is characterized by its ability to function as a solvent for the alkylaromatic products. Solvents satisfying this requirement can be separately added to the feed to the membrane, if needed, but the preferred carrier solvents constitute the unreacted aromatic starting material of the alkylation process, no added solvent being required. Solvent can be added to make up for solvent lost in previous permeations when cascade permeation through multiple membrane units or elements is practiced.

The separation process of the present invention preferably employs an asymmetric polyimide membrane.

Polyimide polymer membranes produced from various polyimide polymers and the use of such membranes to effect various types of aqueous separations and organic liquid separations are presented in numerous patents. See for example, U.S. Pat. No. 4,307,135, U.S. Pat. No. 3,708,458, U.S. Pat. No. 3,789,079, U.S. Pat. No. 3,546,175, U.S. Pat. No. 3,179,632, U.S. Pat. No. 3,179,633, U.S. Pat. No. 3,925,211, U.S. Pat. No. 4,113,628, U.S. Pat. No. 3,816,303, U.S. Pat. No. 4,240,914, U.S. Pat. No. 3,822,202, U.S. Pat. No. 3,853,754, G.B. Pat. No. 1,434,639.

In copending application, U.S. Ser. No. 494,543, filed May 13, 1983, and its continuation-in-part application U.S. Ser. No. 564,302 filed Dec. 22, 1983, a process for producing an asymmetric polyimide polymer membrane from a fully imidized, highly aromatic polyimide copolymer and the use of such membrane for the separation of mixtures of organic liquids is described. The asymmetric polyimide membrane described therein is the membrane of choice for use in the present process. As recited in U.S. Ser. No. 494,543 and U.S. Ser. No. 564,302, the polyimide copolymer starting material is in undegraded form (i.e., copolymer which was not in contact with water for too long a time after production and prior to drying and granulation) and is preferably recovered from commercially available solutions of the copolymer in solvent by use of an organic anti-solvent. Upjohn 2080 DHV, which contains about 25% polymer in DMF solvent, is a suitable source. The copolymer itself is the subject of U.S. Pat. No. 3,708,458 and is the cocondensation product of benzophenone 3,3',4,4'-tetracarboxylic acid dianhydride (BTDA) and a mixture of di(4-amineo-phenyl)methane and toluene diamine, or their corresponding diisocyanates, 4,4'-methylenebis(-phenyl isocyanate) and toluene diisocyanate. As described in U.S. Ser. No. 494,543, and U.S. Ser. No. 564,302, for example, one liter of Upjohn 2080 DHV is transferred to a blender and three successive 300 ml portions of acetone are added with 5 min. mixing at low speed between each addition. Subsequently, the blender contents are emptied into a container and permitted to settle. The liquid is decanted and 1.5 liters of acetone added and the mixture stirred thoroughly. The mixture is filtered through a course filter (Whatman #4). The polymer is washed by remixing with another 2 liters of acetone. After filtering the polymer is dried in vacuum (15 inches Hg) at 45°–60° C. for 3 hours. The polymer powder is ready for use.

As described in U.S. Ser. No. 494,543, and U.S. Ser. No. 564,302 a suitable asymmetric membrane can be cast from this polymer using a casting solution comprising 14–30 weight percent (preferably about 16–25 weight percent more preferably 18–22 weight %) polymer in dioxane:DMF solvent (10:1 to 1:1 D/DMF preferably about 7:1 to 3:1 D/DMF). This solution is spread on a moving casting belt at a casting speed of about 3–5 ft/min. and the film allowed to partially evaporate in dry air, preferably for about 2–120 seconds more preferably about 2–30 seconds before gelation in a gelation bath, which is preferably water (neutral pH). The gelation water is preferably replaced with glycerin to retard membrane deterioration (hydrolysis).

In practicing this process, the membrane can be employed as an element in any convenient form. Membranes in the form of tubes or filters can be bundled, potted and manfolded, much in the manner described in U.S. Pat. No. 3,228,877. Similarly, membranes in the form of sheets can be employed in plate and from configuration or they can be fabricated into a spiral-wound element. Spiral wound element configurations are generally described in U.S. Pat. No. 3,417,870, U.S. Pat. No. 3,173,867, U.S. Pat. No. 3,367,574, U.S. Pat. No. 3,386,583 and U.S. Pat. No. 3,397,790, to list just a few.

The spiral wound element will typically comprise layers of membrane wound around a central tube (metal or solvent resistant plastic) containing holes for the permeate, the membrane layers being separated by alternate layers of a permeate carrier, such as knitted Simplex (Dacron, with malamine formaldehyde stiffener), and a feed spacer made of Vexar (a polypropylene mesh). Membrane layers are typically sealed using an epoxy adhesive to sandwich the permeate cloth into a closed envelope in fluid communication with the perforated central tube leaving the perforations in the central tube as the only permeate outlet. The preferred expoy adhesive will generally comprise resin formulation such as one comprising (1) Epon 828, which is a reaction product of bisphenol-A and epichlorohydrin; (2) Cabosil M5; (3) Versamid 140 (a polyamide curing agent); and (5) DMF solvent wherein the components 1/2/3/4/5 are present in typical relationship based on parts by weight of about 100/10/60/4/12, which cures at about 25° C. over a 21 day period. This adhesive system is described and claimed in copending application, U.S. Ser. No. 494,409, filed May 13, 1983, now U.S. Pat. No. 4,464,494. The layers of membrane, permeate carrier, and feed spacer are wound around the central tube in a fashion consistent with preparing a spiral wound element. After the element is cured, the ends of the element are trimmed, a nylon seal carrier and a nylon anti-telescoping device are then added. The element is then covered on the outside with an epoxy reinforced fiberglass outerwrap. Elements of any size can be prepared, but typical elements are about 8 inches in diameter and about 40 inches long, and have about 225 square feed of membrane area and can be used at feed flow rates of about 30–50 gallons per minute at a 5–15 psi pressure drop.

FIG. 1 presents a schematic of the process of the present invention.

Aromatic hydrocarbons and alkylating agents (such as olefins) are introduced via lines (1A) and (1B) into the alkylation reactor (2). The resulting mixed stream containing the alkylated aromatic products, olefin dimer and unreacted aromatics and olefins (aromatics and olefins identified as "solvent") are passed from reactor 2 through line (3) to a membrane separation unit (4) wherein the stream is contacted with the selective separation membrane preferably under reverse osmosis conditions. A retentate stream made up of the alkylaromatic and olefin dimer (and minor quantities of aromatic and olefin hydrocarbon) is passed via line (5) to the alkylate product separation means (6) wherein a purified alkylate product is recovered (by line 7) and the separated solvent is recovered by line (8) and recycled to the alkylation process reactor. The permeate rich in aromatic and olefin hydrocarbons and enriched in terminal alkylated product from membrane unit (4) is recovered via line (9) and sent to a separator (10) to recover aromatic and alkylating agent from the terminal alkylaromatic isomer (as by, for example, distillation) and the recovered aromatic and alkylating agent are either in whole or in part recycled to the alkylation process (line 11) and/or sent to the motor gas pool (line 12), with the recovered terminal alkylaromatic isomer product being sent via line (13) for storage, use or further processing (not shown).

EXAMPLES

The alkylate was prepared by combining toluene with α-n-hexadecene at a 5:1 molar ratio in the presence of Ketjen HA1.5E catalyst (an amorphous acidic silica alumina) in a continuous laboratory reactor at 180 PSIG of $H_2$, 1.5 cu ft ($H_2$/hr, WHSV of 1.0 $hr^{-1}$ (g olefin:g catalyst) at 120° C. This alkylation procedure is described in detail and claimed in copending application U.S. Ser. No. 603,034 filed even date herewith.

EXAMPLE A

The asymmetric polyimide membranes used to demonstrate the integrated process of the present invention were prepared as follows:

Membrane A: Twenty percent of undegraded granular Upjohn 2080 D polyimide polymer was dissolved in a casting solvent system containing 2:1 dioxane/dimethylformamide. This casting solution was cast onto a backing and permitted to evaporate for 10 to 15 seconds before being gelled in a water bath (tap water) at room temperature.

Membrane B: Twenty percent of undegraded granular Upjohn 2080 D polyimide polymer (see Membrane A above) was dissolved in a casting solvent system containing 5:1 dioxane/dimethylformamide. The casting solution was cast onto a glass plate and permitted to evaporate for 2 seconds before being gelled in a water bath (tap water) at room temperature.

These asymmetric polyimide membranes were then employed in the form of film discs mounted in a membrane holder. The membrane discs were pretreated by successively permeating methyl ethyl ketone and toluene through the membrane at 400 psig and about 23° C. The product stream from an alkylation process as described above was contacted with the asymmetric membrane (dense skin side) at 400 psig at about 23° C.

The results are presented below (see Table 1). The percent rejection is defined by defining toluene and the $C_{16}$ olefins as the solvent and the mono and di alkylate and the olefin dimer as the solute.

TABLE 1

| Membrane | | Wt. % Toluene | Wt. % Olefin | Wt. % Monoalkylate | Olefin Dimer | Wt. % Dialkylate | % R | Flux ($m^3/m^2$ d) |
|---|---|---|---|---|---|---|---|---|
| M-1 | Feed | 54.7 | 12.4 | 23.9 | 3.0 | 6.0 | 54.7 | 0.06 |
| | Perm | 70.3 | 14.8 | 8.4 | 1.85 | 4.6 | | |
| M-2 | Feed | 55.3 | 11.5 | 23.8 | 2.4 | 7.0 | 69.0 | 0.115 |
| | Perm | 80.9 | 8.8 | 5.4 | 2.5 | 2.4 | | |
| M-3 | Feed | 52.7 | 13.5 | 26.8 | 1.8 | 5.2 | 45.1 | 0.135 |
| | Perm | 67.1 | 14.4 | 14.9 | 1.0 | 2.6 | | |
| M-4 | Feed | 52.4 | 12.5 | 26.6 | 1.7 | 6.7 | 36.6 | 0.130 |
| | Perm | 63.90 | 13.8 | 15.7 | 1.4 | 5.1 | | |
| M-5 | Feed | 54.3 | 11.9 | 26.2 | 1.8 | 5.8 | 60.9 | 0.025 |
| | Perm | 70.5 | 16.3 | 9.7 | 1.3 | 2.1 | | |
| M-6 | Feed | 66.9 | 3.1 | 24.2 | 1.5 | 4.3 | 68.8 | 0.075 |
| | Perm | 88.1 | 2.5 | 6.3 | 1.0 | 2.1 | | |

M1 to M4 are Membrane A
M5 to M6 are Membrane B

From this it is seen that aromatic hydrocarbons and olefins selectively permeate through the asymmetric membrane while the alkylate products and olefin dimer are retained. Thus, an alkylate enriched stream is produced which reduces the amount of distillation required to produce the desired purified end product stream.

EXAMPLE B

Use of Asymmetric Polyimide Membranes Enriches the Concentration of the 2-alkylaromatic Isomer in the Permeate This example shows that asymmetric polyimide membranes enrich the concentration of the 2-alkylaromatic isomer in the permeate and deplete the concentration of the 2 isomer in the concentrate. A membrane was prepared in the laboratory from a casting dope containing 20% Upjohn 2080 polyimide polymer, 13% dimethyl formamide and 67% dioxane. The polyimide polymer used was an undeteriorated granular polyimide polymer. The casting solution was cast onto a glass plate and permitted to evaporate for about 2 seconds before being gelled in a room temperature bath of tap water. The membrane was used in the form of film discs mounted in a membrane holder and pretreated as previously described. Feed from a laboratory alkylation unit alkylating toluene with normal $C_{16}$ olefins was used. Alkylation was performed as described above.

The feed to the membrane contained a mixture of α-n-hexadecene, toluene, monoalkylated toluene, olefin dimer and dialkylated toluene. Contacting with the membrane was conducted at 500 psig at 23° C.

Overall, the alkylaromatics are substantially rejected by the membrane yielding a permeate rich in unconverted, recovered aromatic and alkylating agent starting material but containing a minor quantity of copermeated alkylaromatic product (See Table 2). However, the monoalkyl aromatics which are present in the permete have a significantly different concentration of the 2-isomer (terminal isomer) compared to monoalkylaromatics in the feed stream as illustrated in Table 3.

TABLE 2

| Sample | Wt. % Toluene | Wt. % Olefin | Wt. % Monoalkylate | Wt. % Olefin Dimer | Wt. % Dialkylate | Flux (m³/m² d) |
| --- | --- | --- | --- | --- | --- | --- |
| Feed | 54.0 | 12.1 | 26.3 | 1.8 | 5.7 | 0.053 |
| Perm | 78.6 | 14.6 | 6.8 | 0 | 0 | |

TABLE 3

| | Composition of Monoalkylate | | |
| --- | --- | --- | --- |
| Sample | Wt. % 2-isomer | Wt. % 3–8 Isomers | % Rejection |
| Feed | 44.7 | 55.3 | 43.7 |
| Perm | 68.8 | 31.2 | |

$$\% \text{ rejection} = \frac{(\text{wt. \% 3 to 8 isomer) feed} - (\text{wt. \% 3 to 8 isomer) perm}}{(\text{wt. \% 3 to 8 isomer) feed}} \times 100$$

It is thus shown that permeation through an asymmetric polyimide membrane significantly enriches the concentration of the 2-isomer in the permeate stream.

What is claimed is:

1. A method for separating alkylaromatic from a stream comprising a mixture of said alkylaromatics, unconverted aromatic and alkylating agent starting material and coproduced by-product by contacting said mixed stream with a perm-selective asymmetric membrane under reverse osmosis conditions, whereby the unconverted aromatic and alkylating agent starting materials permeate through the asymmetric membrane yielding a permeate stream rich in such unconverted starting material and containing a quantity of co-permeated alkylaromatic material and a retentate steam rich in alkylaromatic product and by-product and lean in the aromatic and alkylating agent starting material.

2. The method of claim 1, wherein the asymmetric membrane is an asymmetric polyimide membrane.

3. The method of claim 2, wherein the asymmetric polyimide membrane is made from a fully imidized highly aromatic polyimide polymer.

4. The method of claim 1, wherein the reverse osmosis condition employed is a pressure at least sufficient to overcome the osmotic pressure and is an applied pressure in the range between about 100 to 800 psig.

5. The method of claims 1, 2 or 3, wherein the feed is contacted with the membrane at a temperature between about 0° to 100° C.

6. The method of claim 4, wherein the feed is contacted with the membrane at a temperature between about 0° to 100° C.

7. A method for separating a feedstream mixture of alkylaromatic isomers into a permeate stream rich in terminal alkylaromatic isomers and a retentate stream rich in internal alkylaromatic isomers which comprises contacting the stream from an aromatic alkylation reaction containing the mixed alkylaromatic isomers, unconverted starting material and co-permeate by-products with a selective asymmetric membrane under reverse osmosis conditions.

8. The method of claim 7, wherein the selective asymmetric membrane is a polyimide membrane made from a fully imidized, highly aromatic polyimide polymer.

9. The method of claim 7, wherein the reverse osmosis condition employed is a pressure at least sufficient to overcome the osmotic pressure and is an applied pressure in the range between about 100 to 800 psig.

10. The method of claims 7 or 8, wherein the feed is contacted with the membrane at a temperature between about 0° to 100° C.

11. The method of claim 10 wherein the terminal alkylaromatic isomers recovered as the permeate stream are the 2- and 3-alkylaromatic isomers.

12. The method of claims 7 or 8, wherein the alkylaromatic stream which is separated into its isomeric components is the product of the alkylation of aromatic hydrocarbons selected from benzene, toluene, the xylenes, ethylbenzene, tetralin, naphthaline and mixtures thereof, alkylated with a long carbon chain alkylating agent.

13. The method of claim 12 wherein the alkylating agent is a $C_8$ to $C_{20}$ Alpha or random internal olefin.

14. The method of claim 13, wherein the aromatic hydrocarbon is benzene, toluene or ethylbenzene and the alkylating agent is a $C_8$ to $C_{20}$ alpha or random internal normal olefin.

* * * * *